(12) United States Patent
Weiman et al.

(10) Patent No.: US 9,662,224 B2
(45) Date of Patent: May 30, 2017

(54) VARIABLE LORDOSIS SPACER AND RELATED METHODS OF USE

(71) Applicant: Globus Medical, Inc., Audubon, PA (US)

(72) Inventors: Mark Weiman, Coatesville, PA (US); Chad Glerum, Pennsburg, PA (US); Alex Burkhardt, Mt. Joy, PA (US); Kevin Gahman, Douglassville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 14/887,476

(22) Filed: Oct. 20, 2015

(65) Prior Publication Data

US 2016/0038305 A1    Feb. 11, 2016

Related U.S. Application Data

(63) Continuation-in-part of application No. 14/449,428, filed on Aug. 1, 2014, which is a continuation-in-part (Continued)

(51) Int. Cl.
| | |
|---|---|
| *A61F 2/44* | (2006.01) |
| *A61F 2/46* | (2006.01) |
| *A61F 2/30* | (2006.01) |
| *A61F 2/28* | (2006.01) |

(52) U.S. Cl.
CPC ............ *A61F 2/4455* (2013.01); *A61F 2/442* (2013.01); *A61F 2/447* (2013.01); *A61F 2/4425* (2013.01); *A61F 2/4611* (2013.01); *A61F 2/30767* (2013.01); *A61F 2002/2817* (2013.01); *A61F 2002/2835* (2013.01); *A61F 2002/3098* (2013.01); *A61F 2002/30266* (2013.01); *A61F 2002/30405* (2013.01); *A61F 2002/30411* (2013.01); *A61F 2002/30415* (2013.01); *A61F 2002/30482* (2013.01); *A61F 2002/30484* (2013.01); *A61F 2002/30538* (2013.01); *A61F 2002/30556* (2013.01); (Continued)

(58) Field of Classification Search
CPC ..................................................... A61F 2/4611
USPC ........................................... 623/17.11–17.16
See application file for complete search history.

(56) References Cited

U.S. PATENT DOCUMENTS

| | | | |
|---|---|---|---|
| 4,349,921 A | 9/1982 | Kuntz | |
| 4,599,086 A | 7/1986 | Doty | |
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |
| 5,306,310 A | 4/1994 | Siebels | |

(Continued)

FOREIGN PATENT DOCUMENTS

| | | |
|---|---|---|
| DE | 4012622 C1 | 7/1991 |
| DE | 4327054 C1 | 4/1995 |

(Continued)

*Primary Examiner* — Nicholas Plionis

(57) ABSTRACT

An expandable fusion device may include a first endplate and a second endplate. The expandable fusion device may also include first and second ramps configured to mate with both the first and second endplates. An inserter instrument includes an outer shaft having a bore extending longitudinally therethrough and an inner shaft extending through the bore in the outer shaft. The outer shaft is configured to engage the first or second opening in the second ramp, and the inner shaft is configured to engage the corresponding first or second opening in the first ramp to control implant height and/or lordotic angle.

16 Claims, 13 Drawing Sheets

Related U.S. Application Data of application No. 14/175,601, filed on Feb. 7, 2014, now Pat. No. 9,402,739.

(52) U.S. Cl.
CPC .............. *A61F 2002/30601* (2013.01); *A61F 2002/30828* (2013.01); *A61F 2002/30843* (2013.01); *A61F 2002/30904* (2013.01); *A61F 2002/4475* (2013.01); *A61F 2310/00011* (2013.01); *A61F 2310/00017* (2013.01); *A61F 2310/00023* (2013.01); *A61F 2310/00179* (2013.01); *A61F 2310/00407* (2013.01); *A61F 2310/00796* (2013.01)

(56) References Cited

U.S. PATENT DOCUMENTS

| | | |
|---|---|---|
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochshuler et al. |
| 6,080,193 A | 6/2000 | Hochshuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,554,863 B2 | 4/2003 | Paul et al. |
| 6,562,074 B2 | 5/2003 | Gerbec et al. |
| 6,576,016 B1 | 6/2003 | Hochshuler et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,685,742 B1 | 2/2004 | Jackson |
| 6,692,495 B1 | 2/2004 | Zacouto |
| 6,706,070 B1 | 3/2004 | Wagner et al. |
| 6,752,832 B2 | 6/2004 | Neumann |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 8,123,810 B2 | 2/2012 | Gordon |
| 8,382,842 B2 | 2/2013 | Greenhalgh et al. |
| 8,518,120 B2 | 8/2013 | Glerum et al. |
| 8,628,578 B2 | 1/2014 | Miller et al. |
| 8,647,386 B2 | 2/2014 | Gordon |
| 2002/0010511 A1* | 1/2002 | Michelson ............ A61F 2/4455 623/17.15 |
| 2002/0045945 A1 | 4/2002 | Liu |
| 2003/0171813 A1 | 9/2003 | Kiester |
| 2004/0049271 A1 | 3/2004 | Biedermann |
| 2004/0054412 A1 | 3/2004 | Gerbec et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0058878 A1 | 3/2006 | Michelson |
| 2006/0122701 A1 | 6/2006 | Kiester |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0140207 A1 | 6/2008 | Olmos et al. |
| 2008/0167657 A1 | 7/2008 | Greenhalgh |
| 2008/0183204 A1 | 7/2008 | Greenhalgh et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0179657 A1 | 7/2010 | Greenhalgh et al. |
| 2012/0029641 A1* | 2/2012 | Curran ................ A61F 2/447 623/17.16 |
| 2014/0031936 A1 | 1/2014 | Weiman |

FOREIGN PATENT DOCUMENTS

| | | |
|---|---|---|
| EP | 0576379 B1 | 6/1993 |
| EP | 0610837 B1 | 7/1994 |
| SU | 1424826 A1 | 9/1988 |
| WO | 9201428 A1 | 2/1992 |
| WO | 9525485 A1 | 9/1995 |

* cited by examiner

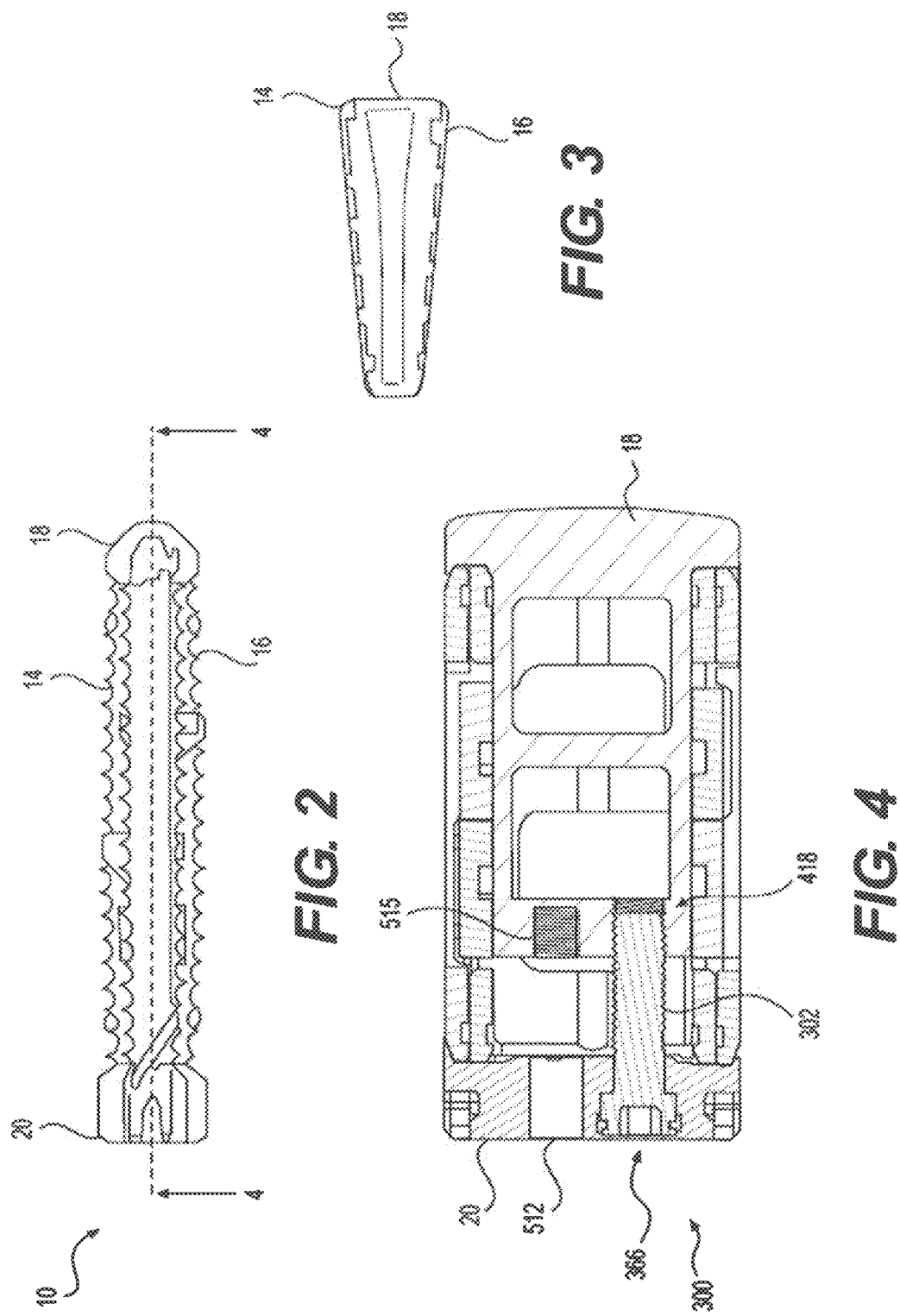

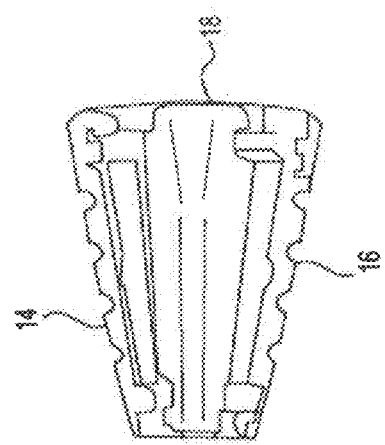
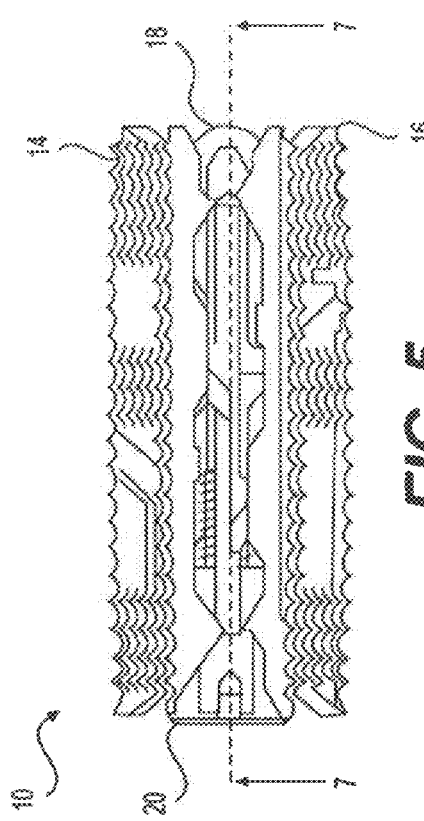
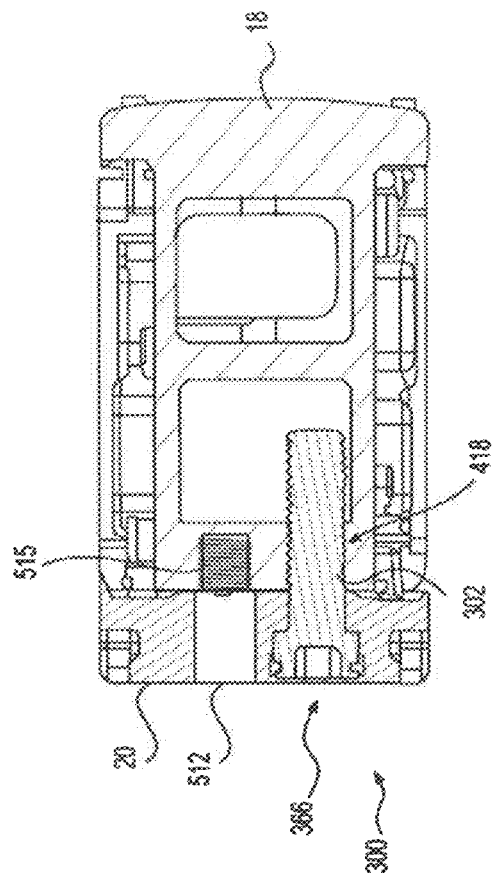

VARIABLE LORDOSIS SPACER AND RELATED METHODS OF USE

CROSS REFERENCE TO RELATED APPLICATION

This application is a continuation-in-part of U.S. application Ser. No. 14/449,428, filed Aug. 1, 2014, which is a continuation-in-part of U.S. application Ser. No. 14/175,601 filed Feb. 7, 2014, the contents of which are hereby incorporated by reference in their entireties for all purposes.

FIELD OF THE INVENTION

Various embodiments of the present disclosure relate generally to variable lordosis spacers and related systems and methods. More specifically, the present disclosure relates to devices, systems, and methods for correcting lordosis and/or other spinal abnormalities.

BACKGROUND

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

Further, lordosis refers to a curvature of the spine, and in particular a curvature that is posteriorly concave. In certain patients, this curvature may, for example, be larger than desired. Traditional vertebral fusion procedures and devices do not adequately account for this curvature. As such, traditional devices do not properly align with adjacent vertebral bodies. To ensure proper fit of traditional devices, bone may be removed from the vertebral bodies, increasing procedure and healing time.

As such, there exists a need for a fusion device capable of being installed inside an intervertebral disc space at a minimum distraction height and for a fusion device that can maintain a normal distance between adjacent vertebral bodies when implanted.

SUMMARY OF THE DISCLOSURE

The present disclosure relates to embodiments of expandable fusion devices and related methods of use.

In one aspect, the present disclosure is directed to an expandable fusion device that may include a first endplate, and a second endplate. The expandable fusion device also may include a first ramp configured to mate with both the first and second endplates. The first ramp may be a wedge with an incline extending along a longitudinal axis of the expandable fusion device, and also may be a wedge having an incline extending along a lateral axis of the expandable fusion device. A second ramp may be configured to mate with both the first and second endplates. The second ramp may be a wedge having an incline extending along the longitudinal axis of the expandable fusion device, and also may be wedge having an incline extending along the lateral axis of the expandable fusion device.

Various examples of the present disclosure may include one or more of the following aspects: wherein the first and second endplates may each include at least one first mating feature configured to mate with at least one corresponding first mating feature disposed on the first ramp; wherein the at least one mating feature of the first and second endplates may be slidable with respect to the corresponding first mating feature disposed on the first ramp; wherein the first and second endplates may each include a second mating feature configured to mate with a corresponding second mating feature disposed on the first ramp; wherein the second mating feature and the corresponding second mating feature may each be C-shaped, V-shaped, or U-shaped; wherein the first and second endplates may each include a third mating feature configured to mate with a corresponding third mating feature disposed on the second ramp; wherein the third mating feature and the corresponding third mating feature may each be C-shaped, V-shaped, or U-shaped; wherein each of the first and second endplates may have an inner surface configured to mate with the first ramp, wherein the inner surface of each of the first and second endplates may be shaped as a concave curve, the concave curve being formed about a longitudinal axis of the expandable fusion device; wherein the expandable fusion device may be movable between a collapsed configuration and an expanded configuration; wherein the first ramp may be coupled to the second ramp by an actuating mechanism, and the expandable fusion device may be configured to transition from the collapsed configuration to the expanded configuration via actuation of the actuating mechanism to move the second ramp and the first ramp toward one another; wherein, in the expanded configuration, the expandable fusion device may be a wedge having an incline extending along the lateral axis of the expandable fusion device; and wherein the first and second endplates each may have an outer surface configured to contact a respective vertebral body, wherein each outer surface of the first and second endplates may have one or more of teeth, ridges, friction increasing elements, keels, or gripping or purchasing projections.

In another aspect, the present disclosure may be directed to an expandable fusion device. The expandable fusion device may include a first endplate and a second endplate, and both the first and second endplates may extend from a first side of the expandable fusion device to a second side of the expandable fusion device. The expandable fusion device also may include a first ramp and a second ramp. Both the first ramp and the second ramp may be configured to mate with both the first and second endplates, and both the first ramp and the second ramp may extend from the first side of the expandable fusion device to the second side of the expandable fusion device. At least one of the first and second sides of the expandable fusion device may pivotally expand about a pivot point.

Various examples of the present disclosure may include one or more of the following aspects: wherein both of the first and second sides of the expandable fusion device may pivotally expand about the same pivot point; wherein the same pivot point may be a point disposed outside of the expandable fusion device; wherein the pivot point may be disposed along the first side or between the first and second sides of the expandable fusion device; and wherein only the second side of the expandable fusion device may pivot about the pivot point.

In yet another aspect, the present disclosure may be directed to an expandable fusion device. The expandable fusion device may include a first endplate and a second endplate, and both the first and second endplates may extend from a first side of the expandable fusion device to a second side of the expandable fusion device. The expandable fusion device also may include a first ramp and a second ramp, and both the first ramp and the second ramp may be configured to mate with both the first and second endplates, and both the first ramp and the second ramp may extend from the first side of the expandable fusion device to the second side of the expandable fusion device. The first and second side of the expandable fusion device may form concentric arcs about a pivot point.

Various examples of the present disclosure may include one or more of the following aspects: wherein the expandable fusion device may be movable between a collapsed configuration and an expanded configuration, and both of the first and second sides of the expandable fusion device may have same angular rate of change when moving between the collapsed configuration and the expanded configuration; and wherein the first side of the expandable fusion device may be defined by a first radius, the second side of the expandable fusion device may be defined by a second radius, and the first radius may be smaller than the second radius.

In yet another aspect, the present disclosure may be directed to an expandable fusion device having a first endplate and a second endplate. The first and second endplates may each include at least one mating feature. A first ramp may be configured to mate with both the first and second endplates, and the first ramp may include a mating feature having a first angle relative to a vertical axis. The mating feature of the first endplate and/or second endplate is slidable with respect to the corresponding mating feature disposed on the first ramp. A second ramp may be configured to mate with both the first and second endplates, and the second ramp may include a mating feature having a second angle relative to the vertical axis. The first angle may be the same or different from the second angle. If different, the first angle may be larger or smaller than the second angle. It may be preferred that the second angle is smaller than the first angle.

Various examples of the present disclosure may include one or more of the following aspects: wherein the first angle is greater than the second angle; wherein the first angle is about 50-70'; wherein the first angle is about 60°; wherein the second angle is about 5-25°; wherein the second angle is about 15°; wherein the first and second ramps are configured to provide for symmetrical expansion of the first and second endplates; wherein at least a portion of the first ramp includes a curved ramp surface; and wherein at least a portion of the first ramp has a continuously changing ramp angle.

In yet another aspect, the present disclosure may be directed to a system comprising an expandable fusion device described herein and an inserter instrument. The inserter instrument may include an outer shaft having a bore extending longitudinally therethrough, and an inner shaft extending through the bore in the outer shaft. The outer shaft may be configured to engage an opening in the second ramp, for example, via threaded engagement. The inner shaft may be configured to engage a corresponding opening in the first ramp, for example, via threaded engagement. By rotating and/or axially moving the inner shaft relative to the outer shaft of the inserter instrument, a change in height and/or lordotic angle of the expandable fusion device may be obtained.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIG. 2 is a longitudinal side view of an embodiment of an expandable fusion device in a first configuration according to the present disclosure.

FIG. 3 is a lateral side view of the expandable fusion device of FIG. 2.

FIG. 4 is a cross-sectional view of the expandable fusion device of FIG. 2 taken along line 4-4.

FIG. 5 depicts the expandable fusion device of FIG. 2 in a second configuration.

FIG. 6 is a lateral side view of the expandable fusion device of FIG. 5.

FIG. 7 is a cross-sectional view of the expandable fusion device of FIG. 5 taken along line 7-7.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
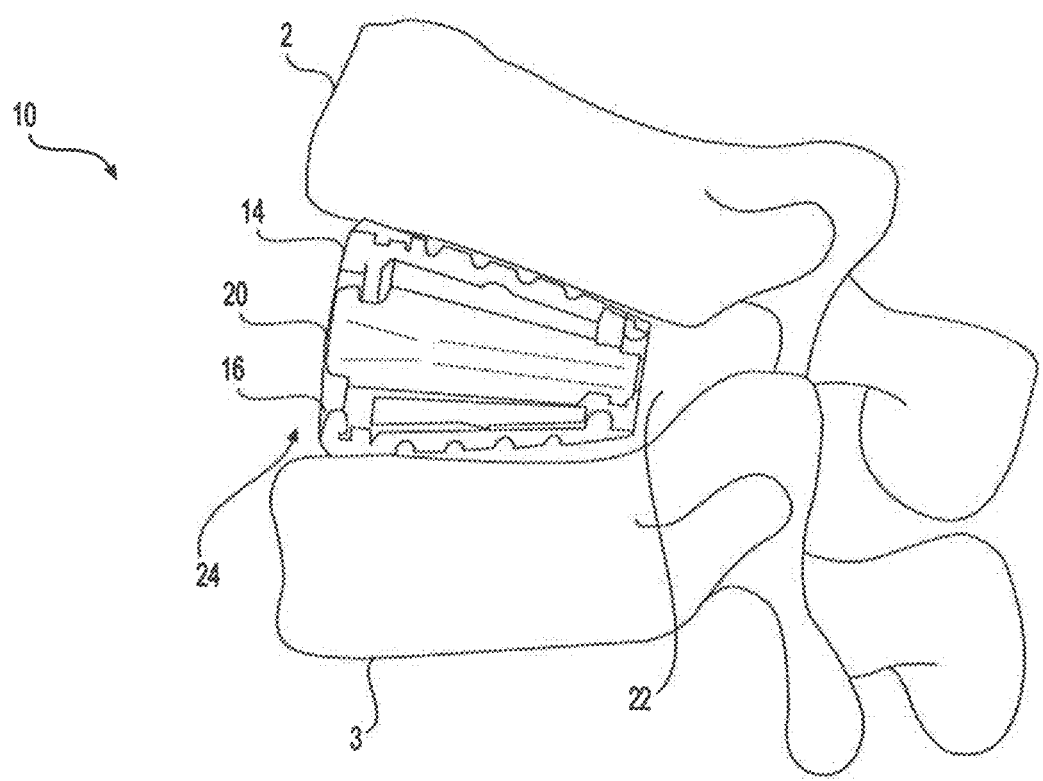
FIG. 1 is a side view of an embodiment of an expandable fusion device shown between adjacent lordotic vertebrae according to the present disclosure.

A spinal fusion is typically employed to eliminate pain caused by the motion of degenerated disk material. Upon successful fusion, a fusion device becomes permanently fixed within the intervertebral disc space. Referring to FIG. 1, an expandable fusion device 10 is shown between adjacent vertebral bodies 2 and 3. Expandable fusion device 10 may extend from a first side 22 (e.g., a posterior side) to a second side 24 (e.g., an anterior side). Expandable fusion device 10 may engage the endplates of adjacent vertebral bodies 2 and 3 and, in an installed position, maintain normal intervertebral disc spacing and restore spinal stability, thereby facilitating an intervertebral fusion. In some embodiments, expandable fusion device 10 may provide indirect decompression (e.g., by reducing the pressure of vertebral bodies 2 and 3 on adjacent nerves) while still providing lordosis correction. Expandable fusion device 10 may be formed from any suitable material or combination of materials, including, but not limited to, titanium, stainless steel, titanium alloys, non-titanium metallic alloys, polymeric materials, plastics, plastic composites, polyetheretherketone (PEEK), ceramic, and elastic materials, among others.

In an embodiment, the expandable fusion device 10 may be configured and sized to be placed down an insertion tube and into the disc space between the adjacent vertebral bodies 2 and 3. For example, expandable fusion device 10 may be configured for insertion through an insertion tube, such as, e.g., a cannula. It should be noted, however, that the insertion tube may alternatively have any suitable diameter. In one embodiment, expandable fusion device 10 may be inserted through a cannula having a diameter of about 8.5 mm. In some embodiments, the expandable fusion device 10 may have a width in a range of from about 8 mm to about 26 mm, and a length in a range from about 20 mm to about 65 mm, or may have other suitable dimensions. Expandable fusion device 10 may be inserted into a patient via a direct lateral procedure, although anterior, anterolateral, posterolateral or posterior procedures alternatively may be utilized.

Expandable fusion device 10 may be generally wedge shaped, and may have a height that increases from first side 22 toward second side 24. In some embodiments, the expandable fusion device 10 may be expanded to a height that is equal to or greater than about 150% of its initial height. In one embodiment, the expandable fusion device 10 may be expanded to a height that is equal to or greater than about 200% of its initial height, or another suitable percentage of its initial height.

Figure 10:
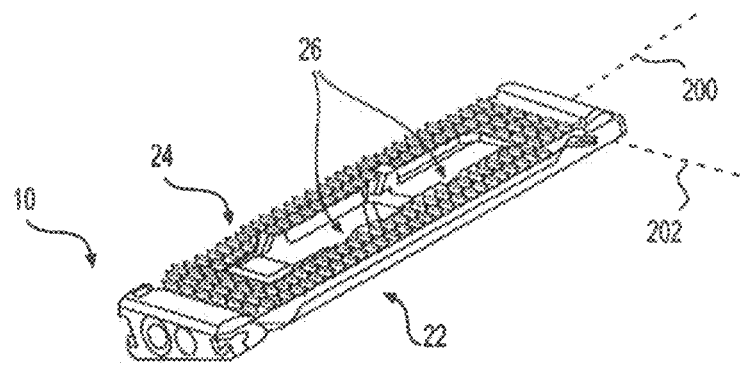
FIG. 10 is a perspective view of the expandable fusion device of FIG. 2.

As shown in FIG. 10, expandable fusion device 10 may include one or more openings 26 to accommodate bone growth along the longitudinal length of the expandable fusion device 10. In some embodiments, openings 26 may have the same dimensions, or may alternatively have different dimensions. In the embodiment shown, expandable fusion device 10 has two openings 26, although other suitable numbers and dimensions of openings are also contemplated. Openings 26 may be sufficiently large to facilitate bone growth after installation of expandable fusion device 10 between vertebral bodies 2 and 3.

In an exemplary embodiment, bone graft or similar bone growth inducing material may be introduced around and within the expandable fusion device 10 to further promote and facilitate the intervertebral fusion. The expandable fusion device 10, in one embodiment, may be packed with bone graft (e.g., autograft or allograft) or similar bone growth inducing material to promote the growth of bone through and around the expandable fusion device 10. The bone graft may be packed between the endplates of the adjacent vertebral bodies prior to, subsequent to, or during implantation of the fusion device.

In one embodiment, expandable fusion device 10 may be treated with a titanium and/or hydroxyapatite plasma spray coating to encourage bony on-growth, improving the strength and stability of the connection between the respective component and the underlying bone (e.g., a vertebral body). Any other suitable coating also may be provided on expandable fusion device 10. Such coatings may include therapeutic agents, if desired. Expandable fusion device 10 also may include radiopaque markings to facilitate in vivo visualization. In some embodiments, portions of expandable fusion device 10 may be formed of a radiolucent material, while other portions of expandable fusion device 10 may be formed of radiopaque materials to facilitate imaging of the radiopaque portions of expandable fusion device 10, such as, e.g., actuating mechanisms, endplates, ramps, or the like.

With reference to FIGS. 2-12, an embodiment of the expandable fusion device 10 is shown. In an exemplary embodiment, the expandable fusion device 10 may include a first endplate 14, a second endplate 16, a first ramp 18, and a second ramp 20. Expandable fusion device 10 may be movable between a collapsed configuration shown in FIGS. 2-4 and 8, and an expanded configuration shown in FIGS. 5-7 and 9. The ability of expandable fusion device 10 to reciprocally move between the collapsed and expanded configurations may provide numerous benefits. For example, because expandable fusion device 10 can be inserted between the vertebral bodies 2 and 3 in a collapsed configuration that is smaller than the expanded configuration, the large impaction forces needed to install traditional fusion devices are not required to install expandable fusion device 10. In one embodiment, expandable fusion device 10 may be in a lordotic state in the collapsed configuration, although other suitable configurations, such as, e.g., parallel or other starting angles, are also contemplated.

Figure 8:
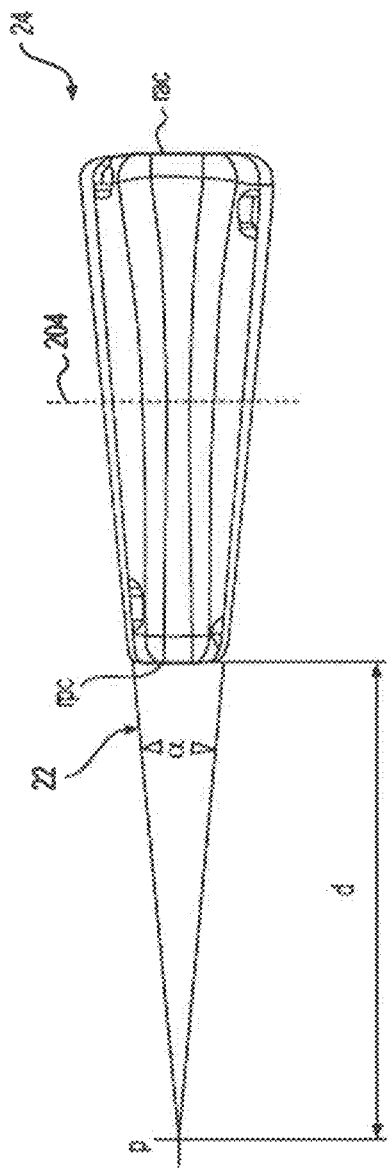
FIG. 8 is a side view of the expandable fusion device of FIG. 2 in the first configuration, showing a pivot point.
Figure 9:
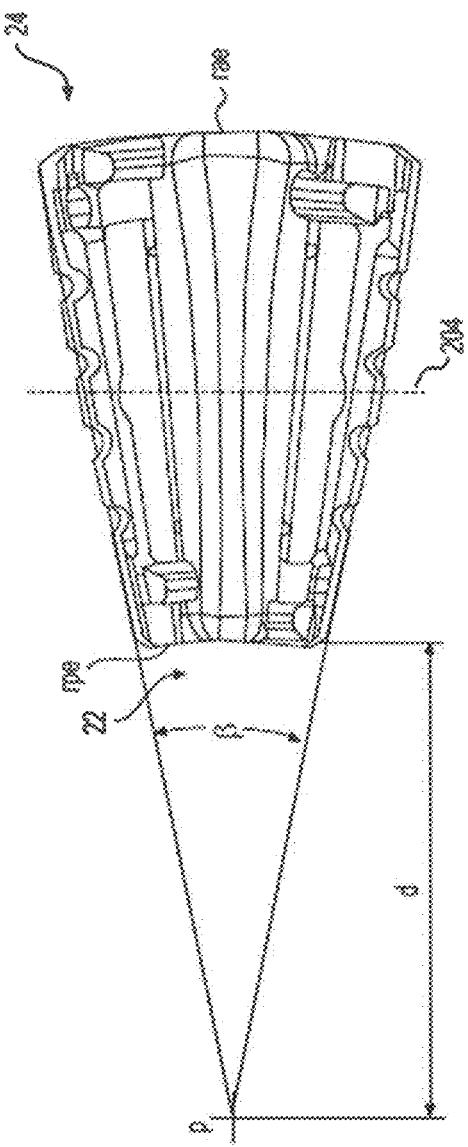
FIG. 9 is a side view of the expandable fusion device of FIG. 2 in the second configuration, showing the pivot point of FIG. 8.

Expandable fusion device 10 may expand and collapse about a set pivot point P, shown in FIGS. 8 and 9. Expandable fusion device 10 may be constructed to alter the position of pivot point P. That is, first ramp 18, second ramp 20, and endplates 14, 16 may be constructed to exhibit a curvature (e.g., may have a radius of curvature) about pivot point P, as further described below. In the collapsed configuration shown in FIGS. 2-4 and 8, expandable fusion device 10 may maintain an angle α (shown only in FIG. 8) with respect to pivot point P. In the expanded configuration shown in FIGS. 5-7 and 9, expandable fusion device 10 may maintain an angle β (shown only in FIG. 9) with respect to pivot point P. The construction of expandable fusion device 10 also may select the rate of change between angles α and β in the transition of expandable fusion device 10 between the collapsed and expanded configurations. In some embodiments, expandable fusion device 10 may experience a linear increase in the lordotic angle during the transition from the collapsed configuration to the expanded configuration (i.e., through an expansion range). In some embodiments, expandable fusion device 10 may be constructed to set pivot point P closer to the expandable fusion device 10 (or even within the perimeter of expandable fusion device 10). As pivot point P moves toward expandable fusion device 10 (or further toward a midline 204 shown in FIGS. 8 and 9), the rate of angle change per height change exhibited by expandable fusion device 10 may increase. Because second side 24 has a larger distance from pivot point P than first side 22, second side 24 may increase in height faster than first side 22 in the transition of expandable fusion device 10 from the collapsed configuration to the expanded configuration. Thus, expandable fusion device 10 may be constructed in various configurations to set different α and β angles (i.e., different ramp angles on the anterior and posterior sides of expandable fusion device 10).

The position of pivot point P may be dependent or independent upon the inclination of expandable fusion device 10 between first side 22 and second side 24. That is, as the difference in height between first side 22 and second side 24 increases, pivot point P may be set closer to expandable fusion device 10, or even within the perimeter of expandable fusion device 10. Thus, as pivot point P is set closer to expandable fusion device 10 (or further toward midline 204), angles α and β may become larger. On the contrary, as the pivot point P is set further from expandable fusion device 10, a smaller rate of angle change per height change, and smaller α and β angles will be present in expandable fusion device 10.

In one embodiment, α may be about 10.4°, β may be about 22.5°, and a distance d between pivot point P and first side 22, may be about 17 mm although other suitable values are also contemplated.

First and second sides 22, 24 of expandable fusion device 10 may thus be formed as arcs (e.g., concentric arcs) about pivot point P. In the collapsed configuration, first side 22 may be oriented at angle α with respect to pivot point P, and may have a radius $r_{pc}$. In the collapsed configuration, second side 24 also may be oriented at angle α with respect to pivot point P, but may have a radius $r_{ac}$ that is larger than radius $r_{pc}$, as second side 24 may be oriented at a further distance from pivot point P than first side 22. In the expanded configuration, first and second sides 22, 24 of expandable fusion device 10 may expand at a substantially similar angular rate, and may both become oriented at angle β with respect to pivot point P. In the expanded configuration, first side 22 may have a radius $r_{pc}$ that is constant with radius $r_{pc}$.

The curvatures of first ramp 18, second ramp 20, and endplates 14, 16, may determine the location of pivot point P. As shown in FIGS. 8 and 9, the curvatures of first ramp 18, second ramp 20, and endplates 14, 16 may cause first and second sides 22, 24 of expandable fusion device 10 to be curved about pivot point P to form portions of the aforementioned concentric arcs. The curvature of first and second sides 22, 24, may set the distance of pivot point P from first and second sides 22, 24. That is, if expandable fusion device 10 is constructed so as to position pivot point P relatively farther from first and second sides 22, 24, each of first and second sides 22, 24 may have shallower curvatures. On the contrary, if expandable fusion device 10 is constructed so as to position pivot point P relatively closer to first and second sides 22, 24 (or even between first and second sides 22, 24), each of first and second sides 22, 24 may have steeper curvature.

Figure 11:
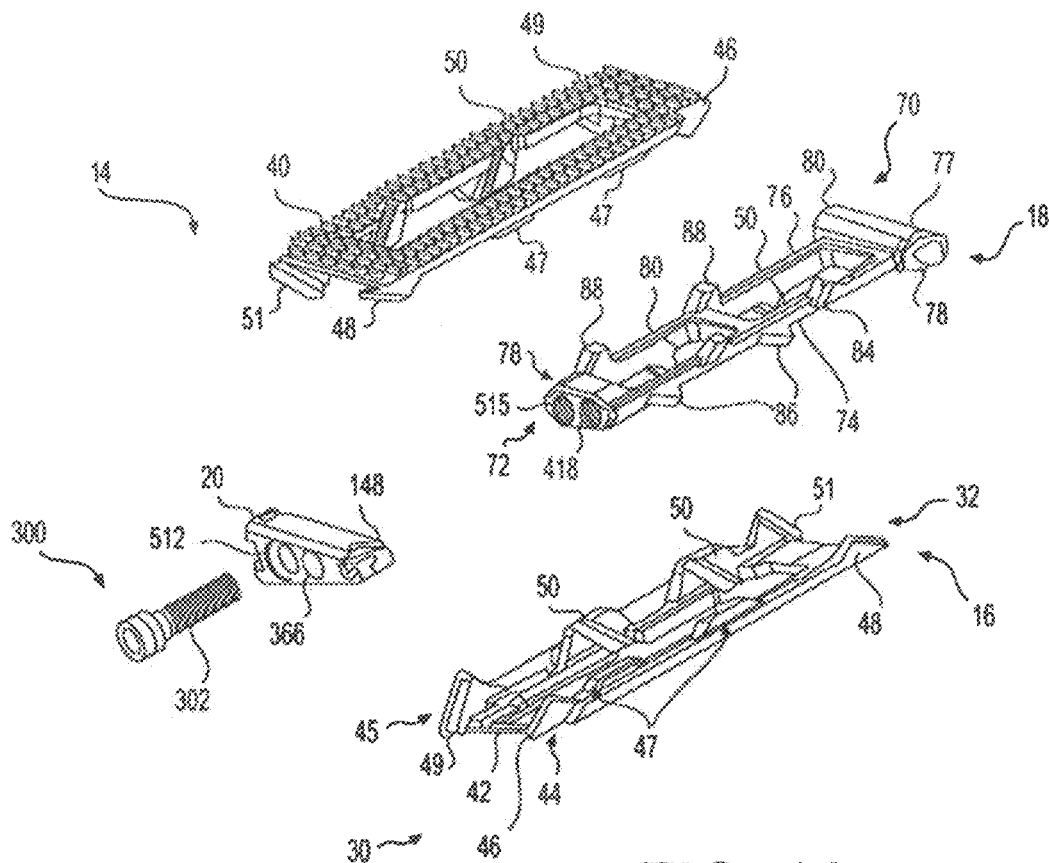
FIG. 11 is an exploded view of the expandable fusion device of FIG. 2.
Figure 12:
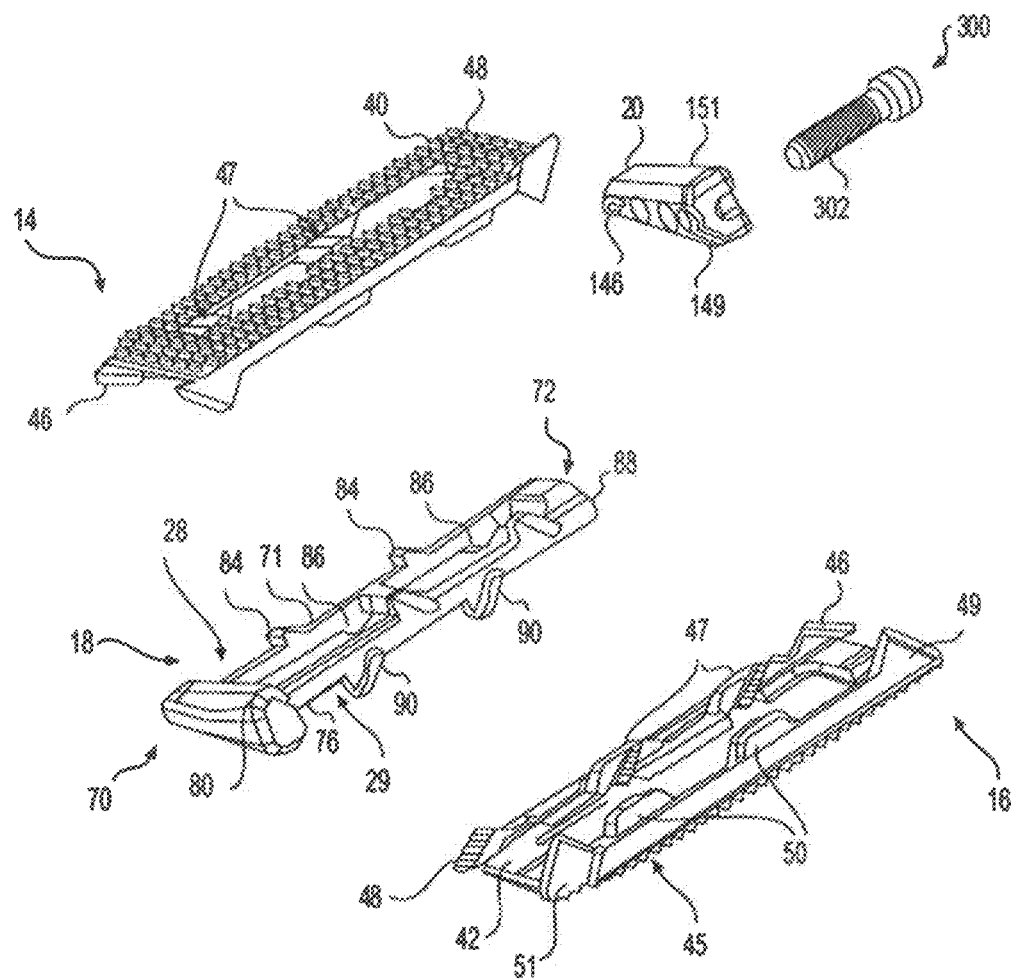
FIG. 12 is another exploded view of the expandable fusion device of FIG. 2.

Referring to FIGS. 11 and 12, endplates 14, 16 may have a first end 30 and a second end 32. In the illustrated embodiment, the endplates 14, 16 may include an outer surface 40 connecting the first end 30 and the second end 32, and an inner surface 42 connecting the first end 30 and the second end 32. Outer surface 40 and inner surface 42 may both be defined by first and second ends 30, 32, and by a first side 44 and a second side 45. First side 44 of endplates 14, 16 may be disposed at first side 22 of expandable fusion device 10. Similarly, second side 45 of endplates 14, 16 may be disposed at second side 24 of expandable fusion device 10. First and second sides 44, 45 may define a plurality of mating features configured to engage with one or more mating features of first ramp 18 and second ramp 20. In one embodiment, both first and second sides 44, 45 may extend from inner surface 42. Second side 45 may extend further from inner surface 42 than first side 44.

First side 44 may include a mating feature 46 at first end 30, at least one mating feature 47 at an intermediate portion, and a mating feature 48 at second end 32.

Mating feature 46 may be substantially C-shaped, V-shaped, U-shaped, or otherwise suitably shaped. In the embodiment shown, mating feature 46 may form a slidable joint with a corresponding mating feature (e.g., one of mating features 77 or 146 described in further detail below). The slidable joint may be, e.g., a tabled splice joint, or another suitable joint. That is, mating feature 46 and its corresponding mating feature 77 or 146 may be similarly shaped to have a groove disposed between two shoulders. One shoulder of mating feature 46 may slide within the groove of the corresponding mating feature 77 or 146, while one shoulder of the corresponding mating feature 77 or 146 may slide within the groove of mating feature 46. In some embodiments, it should be understood that mating feature 46 and its corresponding mating feature 77 or 146 may be formed in any other suitable manner. For example, mating feature 46 and its corresponding mating feature 77 or 146 may form another splice joint, a tongue and groove joint, another suitable joint, or be related to each other in another suitable manner. In some embodiments, mating feature 46 and its corresponding mating feature 77 or 146 may be slidable and/or interlocking with one another. In some embodiments, mating feature 46 may be inclined along longitudinal axis 200 from first end 30 of endplates 14, 16 toward an intermediate portion of endplates 14, 16.

In the embodiment shown by FIGS. 11 and 12, mating features 47 are shown as defining inwardly facing recesses or grooves. The recesses of mating features 47 may accept a protrusion or tongue of a corresponding mating feature (e.g., mating features 84 and 86 described in further detail below). Thus, mating features 47 and its corresponding mating features 84 or 86 may form a tongue and groove joint. That is, the tongue of the corresponding mating feature 84 or 86 may be slidable within the groove of mating feature 47. It is also contemplated that mating feature 47 and its corresponding mating feature 84 or 86 may form another type of joint, such as, e.g., a splice joint, another suitable joint, or be related to each other in another suitable manner. In some embodiments, mating features 47 and their corresponding mating features 84 or 86 may be slidably interlocking with one another. In some embodiments, mating features 47 may be inclined along longitudinal axis 200 from a respective intermediate portion of endplates 14, 16 toward first end 30 of endplates 14, 16. Thus, the inclinations of mating feature 46 and mating features 47 may generally oppose one another. Alternatively, mating features 47 may be inclined in any other suitable direction, such as, e.g., from a respective intermediate portion of endplates 14, 16 toward second end 32 of endplates 14, 16.

Mating feature 48 and its corresponding mating feature (e.g., mating features 78 and 148 described in further detail below) may be substantially similar to mating feature 46 described above. In some embodiments, mating feature 48 may be inclined along longitudinal axis 200 from second end 32 of endplates 14, 16 toward an intermediate portion of endplates 14, 16. Thus, the inclinations of mating features 46 and 48 may oppose one another, but the inclinations of mating features 47 and 48 may be generally aligned (e.g., substantially parallel).

Second side 45 may include a mating feature 49 at first end 30, at least one mating feature 50 at an inner (or intermediate) portion, and a mating feature 51 at second end 32. Mating feature 49 may be similar to mating feature 46 described above, except that mating feature 49 may have different (e.g., larger) dimensions than mating feature 46. Similar to mating feature 46, mating feature 49 may be inclined along longitudinal axis 200 from first end 30 of endplates 14, 16 toward an intermediate portion of endplates 14, 16.

Mating features 50 may be similar to mating features 47, except that mating features 50 may have different (e.g., larger) dimensions than mating features 47. Similar to mating features 47, mating features 50 may be inclined along longitudinal axis 200 from a respective intermediate portion of endplates 14, 16 toward first end 30 of endplates 14, 16. Thus, the inclinations of mating feature 49 and mating features 50 may generally oppose one another. Alternatively, mating features 50 may be inclined in any other suitable direction, such as, e.g., from a respective intermediate portion of endplates 14, 16 toward second end 32 of endplates 14, 16.

Mating feature 51 may be substantially similar to mating feature 46 described above. However, in some embodiments, mating feature 51 may have different (e.g., larger) dimensions than mating feature 46. Similar to mating feature 46, mating feature 51 may be inclined along a longitudinal axis 200 (referring to FIG. 10) from second end 32 of endplates 14, 16 toward an intermediate portion of endplates 14, 16. Thus, the inclinations of mating features 46 and 48 may oppose one another, but the inclinations of mating features 50 and 51 may be generally aligned (e.g., substantially parallel).

Mating features 46-51 may be configured to mate with a corresponding mating feature on one of first and second ramps 18 and 20 in a slidable and/or interlocking relationship.

Outer surface 40 and/or inner surface 42 may be curved about one or more axes. For example, outer surface 40 and/or inner surface 42 may be curved about longitudinal axis 200. Thus, in one embodiment, outer surface 40 may be convex, while inner surface 42 may be concave about the longitudinal axis 200. In some embodiments, material can be added to or removed from outer surface 40 to modify the interaction between outer surface 40 and vertebral bodies 2 and 3. For example, material can be added to give outer surface 40 a generally flat configuration while maintaining the concavity of inner surface 42.

Figure 13:
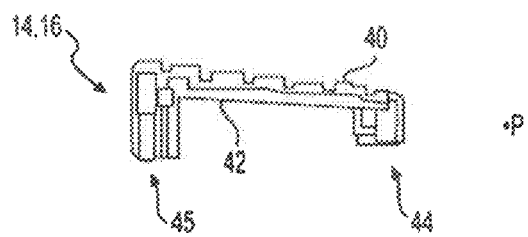
FIG. 13 is a lateral side view of an endplate incorporated into the expandable fusion device of FIG. 12.
Figure 14:
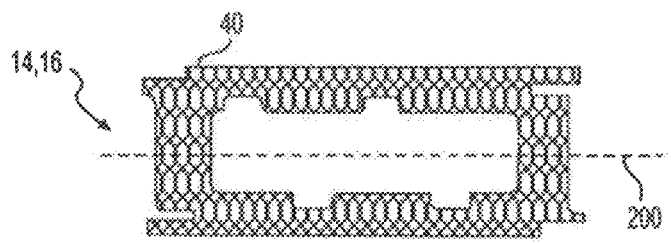
FIG. 14 is a top view of the endplate of FIG. 13.
Figure 15:
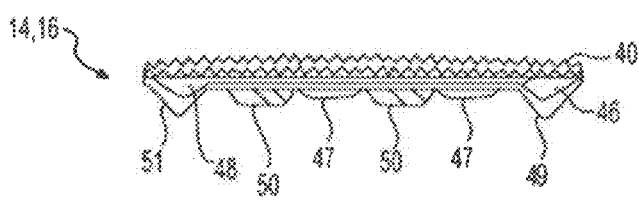
FIG. 15 is a longitudinal side view of the endplate of FIG. 13.

The respective mating features of endplates 14, 16 may be curved in order to impart a curvature to first and second sides 22, 24 of assembled expandable fusion device 10 as set forth above. As best seen in FIG. 13, first and second sides 44 and 45 may be curved (e.g., may have a radius of curvature) about pivot point P, and thus mating features 46-51 that are disposed in one of first and second sides 44, 45 may be similarly curved with respect to pivot point P.

In some embodiments, the outer surface 40 of endplates 14, 16 may be flat and generally planar to allow the outer surface 40 engage with an adjacent vertebral body. Alternatively, the outer surface 40 may be curved convexly or concavely to allow for a greater or lesser degree of engagement with the adjacent vertebral body. It is also contemplated that the outer surface 40 may be generally planar but include a generally straight ramped surface or a curved ramped surface. The ramped surface may allow for engagement with the adjacent vertebral body in a further lordotic fashion. In one embodiment, the outer surface 40 may include texturing to aid in gripping the adjacent vertebral bodies. Although not limited to the following, the texturing may include teeth, ridges, friction increasing elements, keels, or gripping or purchasing projections.

Figure 16:
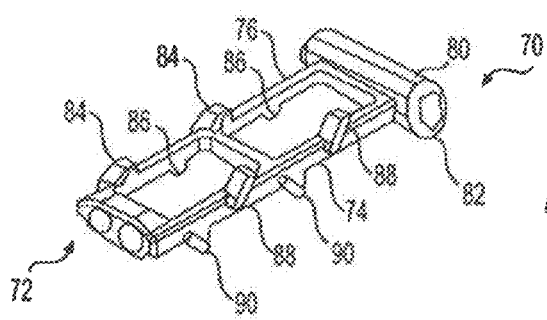
FIG. 16 is a perspective view of a first ramp incorporated into the expandable fusion device of FIG. 12.

Referring now to FIGS. 11, 12, and 16, the first ramp 18 may have a first end 70, a second end 72, a first side portion 74 connecting the first end 70 and the second end 72, and a second side portion 76 on the opposing side of the first ramp 18 connecting the first end 70 and the second end 72. The first ramp 18 may further include a third end (e.g., an upper end) 28, which is sized to receive at least a portion of the first endplate 14, and a fourth end (e.g., a lower end) 29, which is sized to receive at least a portion of the second endplate 16.

The first end 70 of the first ramp 18, in an exemplary embodiment, may include four mating features 77, 78, 80, and 82 (mating feature 82 shown only in FIG. 16). Each of mating features 77, 78, 80, 82 may be shaped to mate with a respective mating feature disposed on one of endplates 14, 16. Mating feature 77 may be configured to mate with, and may be similarly shaped as mating feature 46 of endplate 14. Mating feature 78 may be configured to mate with, and may be similarly shaped as mating feature 48 of endplate 16. Mating feature 80 may be configured to mate with, and may be similarly shaped as mating feature 49 of endplate 14. Mating feature 82 may be configured to mate with, and may be similarly shaped as mating feature 51 of endplate 16. Each of mating features 77, 78, 80, and 82 may have substantially similar inclinations (with respect to an assembled expandable fusion device 10) their respective and corresponding mating features set forth above. In one embodiment, each of mating features 77, 78, 80, and 82 are inclined from an intermediate portion of first ramp 18 toward first end 70 of first ramp 18, although other suitable configurations are also contemplated. In one embodiment, mating features 77 and 78 extend from third end 28, while mating features 78 and 82 extend from fourth end 29.

First side portion 74 may include mating features 84 and 86 that are configured to mate with various mating features of endplates 14, 16.

Mating features 84 may be protrusions extending from an intermediate portion of first side portion 74 toward first end 70. In one embodiment, mating features 84 may have a surface that is inclined from the intermediate portion of first side portion 74 toward first end 70. The inclined surface of mating features 84 also may extend laterally outward from first side portion 74. Mating features 84 also may extend from third end 28 of first ramp 18. The inclined surface of mating features 84 may extend toward a generally flattened surface that is substantially parallel to longitudinal axis 200 of expandable fusion device 10. In one embodiment, first ramp 18 may include at least two mating features 84 that are staggered along first side portion 74, although other suitable numbers of mating features 84 may alternatively be utilized. In the embodiment shown, mating features 84 are substantially similar to one another, although it is contemplated that mating features 84 may be different than one another. Mating features 84 may be configured to mate with mating features 47 of endplate 14. In the embodiment shown in FIGS. 11 and 12, mating features 47 and 84 may form a slidable and interlocking (e.g., a tongue and groove) joint that allows expandable fusion device 10 to move between the collapsed and expanded configurations. However, it is contemplated that mating features 47 and 84 may be modified to other suitable configurations that allow expandable fusion device 10 to move between the collapsed and expanded configurations. For example, in one alternative embodiment, mating features 47 may be formed as protrusions, while mating features 84 are formed as recesses. In another alternative embodiment, each of mating features 47 and 84 may be formed as grooves disposed between two shoulders such that mating features 47 and 84 form a splice joint (e.g., similar to the tabled splice joints described above).

Mating features 86 may be protrusions extending from an intermediate portion of first side portion 74 toward first end 70. In one embodiment, mating features 86 may have a surface that is inclined from the intermediate portion of first side portion 74 toward first end 70. The inclined surface of mating features 86 also may extend laterally outward from first side portion 74. Unlike mating features 84, mating features 86 may extend from fourth end 29 of first ramp 18. Thus, mating features 84 and 86 may extend in generally opposite vertical directions from first side portion 74. The inclined surface of mating features 86 may extend toward a generally flattened surface that is substantially parallel to longitudinal axis 200 of expandable fusion device 10. In one embodiment, first ramp 18 may include at least two mating features 86 that are staggered along first side portion 74, although other suitable numbers of mating features 86 may alternatively be utilized. In some embodiments, each of mating features 84 and 86 may be staggered from one another, although other suitable configurations are also contemplated. In the embodiment shown, mating features 86 are substantially similar to one another, although it is contemplated that mating features 86 may be different than one another. Mating features 86 may be configured to mate with mating features 47 of endplate 16. In the embodiment shown in FIGS. 11 and 12, mating features 47 and 86 may form a slidable and interlocking (e.g., a tongue and groove) joint that allows expandable fusion device 10 to move between the collapsed and expanded configurations. However, it is contemplated that mating features 47 and 86 may be modified to other suitable configurations that allow expandable fusion device 10 to move between the collapsed and expanded configurations (e.g., in a substantially similar manner as described above with reference to mating features 47 and 84).

Second side portion 76 may include mating features 88 and 90 that are configured to mate with various mating features of endplates 14, 16.

Mating features 88 may be protrusions extending from an intermediate portion of second side portion 76 toward first end 70. In one embodiment, mating features 88 may have a surface that is inclined from the intermediate portion of second side portion 76 toward first end 70. The inclined surface of mating features 88 also may extend laterally outward from second side portion 76. Mating features 88 also may extend from third end 28 of first ramp 18. The inclined surface of mating features 88 may extend toward a generally flattened surface that is substantially parallel to longitudinal axis 200 of expandable fusion device 10. In one embodiment, first ramp 18 may include at least two mating features 88 that are staggered along second side portion 76, although other suitable numbers of mating features 88 may alternatively be utilized. In the embodiment shown, mating features 88 are substantially similar to one another, although it is contemplated that mating features 88 may be different than one another. Mating features 88 may be configured to mate with mating features 50 of endplate 14. In the embodiment shown in FIGS. 11 and 12, mating features 50 and 88 may form a slidable and interlocking (e.g., a tongue and groove) joint that allows expandable fusion device 10 to move between the collapsed and expanded configurations. However, it is contemplated that mating features 50 and 88 may be modified to other suitable configurations that allow expandable fusion device 10 to move between the collapsed and expanded configurations (e.g., in a substantially similar manner as described above with reference to mating features 47 and 84).

Mating features 90 may be protrusions extending from an intermediate portion of second side portion 76 toward first end 70. In one embodiment, mating features 90 may have a surface that is inclined from the intermediate portion of second side portion 76 toward first end 70. The inclined surface of mating features 90 also may extend laterally outward from second side portion 76. Unlike mating features 88, mating features 90 may extend from fourth end 29 of first ramp 18. Thus, mating features 88 and 90 may extend in generally opposite vertical directions from second side portion 76. The inclined surface of mating features 90 may extend toward a generally flattened surface that is substantially parallel to longitudinal axis 200 of expandable fusion device 10. In one embodiment, first ramp 18 may include at least two mating features 90 that are staggered along second side portion 76, although other suitable numbers of mating features 90 may alternatively be utilized. In some embodiments, each of mating features 88 and 90 may be staggered from one another, although other suitable configurations are also contemplated. In the embodiment shown, mating features 90 are substantially similar to one another, although it is contemplated that mating features 90 may be different than one another. Mating features 90 may be configured to mate with mating features 50 of endplate 16. In the embodiment shown in FIGS. 11 and 12, mating features 50 and 90 may form a slidable and interlocking (e.g., a tongue and groove) joint that allows expandable fusion device 10 to move between the collapsed and expanded configurations. However, it is contemplated that mating features 50 and 90 may be modified to other suitable configurations that allow expandable fusion device 10 to move between the collapsed and expanded configurations (e.g., in a substantially similar manner as described above with reference to mating features 47 and 84).

Figure 17:
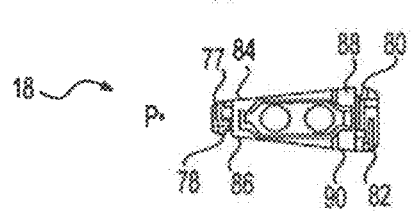
FIG. 17 is a lateral side view of the first ramp of FIG. 16.
Figure 18:
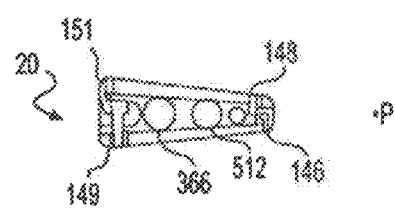
FIG. 18 is a lateral side view of a second ramp incorporated into the expandable fusion device of FIG. 12.

The respective mating features of first ramp 18 may be curved in order to impart the curvature to first and second sides 22, 24 of assembled expandable fusion device 10 as set forth above. That is, the mating features of first ramp 18 may have a radius of curvature about pivot point P. Further, as the mating features of first ramp 18 may be complimentary to corresponding mating features along endplates 14, 16, the mating features of endplates 14, 16 also may have a radius of curvature about pivot point P. Referring to FIG. 17, mating features 77, 78, 80, 82, 84, 86, 88, and 90 may each have a radius of curvature about pivot point P. Thus, all or a portion of first ramp 18 may be bent about pivot point P. The geometry of first ramp 18 (e.g., any of the aforementioned radii of curvature) may be approximated with simpler features for manufacturing ease.

As shown in FIG. 11, first ramp 18 may include both a bore 418 and a bore 515. In some embodiments, the bore 418 may be threaded and configured to receive a threaded member 302 of an actuating mechanism 300. The central longitudinal axis of the bore 418 may be off-center from the central longitudinal axis of the first ramp 18 in order to accommodate the bore 515.

The adjacent bore 515 may serve as an access port to allow graft material to be delivered through the first ramp 18, either prior to insertion or even in situ, if desired. The bore 418 may align with a bore 366 in second ramp 20 and bore 515 may align with an additional bore 512 in the second ramp 20, as discussed below.

Second ramp 20 may be disposed adjacent to first ramp 18 in expandable fusion device 10. Second ramp 20 may include four mating features 146, 148, 149, and 151. Each of mating features 146, 148, 149, and 151 may be substantially similar to mating feature 46 described above, and may be configured to mate with a respective mating feature disposed on one of endplates 14, 16. Mating feature 146 may be configured to mate with mating feature 46 of endplate 16. Mating feature 148 may be configured to mate with mating feature 48 of endplate 14. Mating feature 149 may be configured to mate with mating feature 49 of endplate 16. Mating feature 151 may be configured to mate with mating feature 51 of endplate 14.

The respective mating features of second ramp 20 may be curved in order to impart the curvature to first and second sides 22, 24 of assembled expandable fusion device 10 as set forth above. Further, as the mating features of second ramp 20 may have a radius of curvature about pivot point P, the mating features of endplates 14, 16 also may have a radius of curvature about pivot point P. Mating features 146, 148, 149, and 151 may be all curved about pivot point P. Thus, all or a portion of second ramp 20 may be bent about pivot point P. The geometry of second ramp 20 (e.g., any of the aforementioned radii of curvature) may be approximated with simpler features for manufacturing ease.

In one alternative embodiment, expandable fusion device 10 may be formed so as to locate pivot point P within lateral width of the expandable fusion device 10 along first side 22 of expandable fusion device 10. In this alternative embodiment, all mating features (e.g., tracks, protrusions, grooves, shoulders, and the like) disposed along first side 22 of expandable fusion device 10 (e.g., along endplates 14, 16, and first and second ramps 18 and 20) may be replaced by linkage or pivoting mechanisms. When pivot point P is located within lateral width of the expandable fusion device 10 along first side 22 of expandable fusion device 10, only second side 24 may pivot about pivot point P during expansion and collapse of expandable fusion device 10.

As described above, the second ramp 20 may include a bore 366 adjacent bore 512. The bore 366 may be configured to receive an actuating mechanism 300 therethrough, and may be aligned with the bore 418 in the first ramp 18. Accordingly, the bore 366 may have a central longitudinal axis that is off-set from the central longitudinal axis of the second ramp 20 to accommodate the adjacent bore 512. The bore 512 of the second ramp 20 may be aligned with the bore 515 of the first ramp 18 to allow graft material to be inserted into the implant, either prior to or even after insertion of the implant.

First and second ramps 18 and 20 may each be a wedge having an incline extending in at least two planes. That is, each of first and second ramps 18 and 20 may be a wedge having an incline extending along a plane defined by longitudinal axis 200 (i.e., may be inclined along the longitudinal axis 200), while also being a wedge having an incline extending along a plane defined a lateral axis 202 (i.e., may be inclined along the lateral axis 202). The inclination of first and second ramps 18 and 20 (and their associated mating features) along the longitudinal axis 200 of expandable fusion device 10 may allow for the expansion/compression of endplates 14 and 16 as first and second ramps 18 and 20 translate with respect to one another along the longitudinal axis 200. The inclination of first and second ramps 18 and 20 along the lateral axis 202 of expandable fusion device 10 may accommodate the uneven lengths of first and second sides 44, 45 of endplates 14, 16.

A method of installing the expandable fusion device 10 of FIG. 1 is now discussed in accordance with one embodiment of the present disclosure. Prior to insertion of the expandable fusion device 10, the intervertebral space may be prepared. In one method of installation, a discectomy may be performed where the intervertebral disc, in its entirety, may be removed. Alternatively, only a portion of the intervertebral disc can be removed. The endplates of the adjacent vertebral bodies 2, 3 may be then scraped to create an exposed end surface for facilitating bone growth across the intervertebral space. One or more introduction sheaths then can be inserted into the disc space. The expandable fusion device 10 can then be introduced into the intervertebral space down an insertion sheath and seated in an appropriate position in the intervertebral disc space.

After the expandable fusion device 10 has been inserted into the appropriate position in the intervertebral disc space, the expandable fusion device 10 can then be transitioned from the collapsed configuration to the expanded configuration. To expand the expandable fusion device 10, the second ramp 20 may be moved toward the first ramp 18. As the first and second ramps 18 and 20 move toward one another, the respective mating features of first and second ramps 18 and 20 may push against corresponding mating features disposed on endplates 14 and 16 to move expandable fusion device 10 into the expanded configuration. In some embodiments, one or more of endplates 14, 16, and first and second ramps 18, 20 may include locking features for securing expandable fusion device 10 in the expanded configuration.

In the event the expandable fusion device 10 needs to be repositioned or revised after being installed and expanded, the expandable fusion device 10 can be contracted back to the collapsed configuration, repositioned, and expanded again once the desired positioning is achieved. To contract the expandable fusion device 10, the first ramp 18 is moved away from the second ramp 20 via the actuating mechanism 300.

Actuating mechanism 300 may include any suitable actuating mechanism configured to translate first and second ramps 18 and 20 toward and away from each other along the longitudinal axis 200. Referring to FIGS. 4 and 7, actuating mechanism 300 may include a threaded member 302 (e.g., a screw) that, when rotated in a first direction, directs first and second ramps 18 and 20 toward each other, moving expandable fusion device 10 from the collapsed configuration to the expanded configuration. When threaded member 202 is rotated in a second direction that is opposite to the first direction, first and second ramps 18 and 20 may be moved away from each other, causing expandable fusion device 10 to move back toward the collapsed configuration. In one embodiment, threaded member 302 may be partially disposed through bore 515 of first ramp 18, and may further extend through bore 515 as expandable fusion device 10 is moved from the collapsed configuration to the expanded configuration. In this embodiment, threaded member 302 may push second ramp 20 toward first ramp 18, and may move coextensively with second ramp 20 during the transition of expandable fusion device 10 from the collapsed configuration to the expanded configuration and from the expanded configuration to the collapsed configuration.

Figure 19:
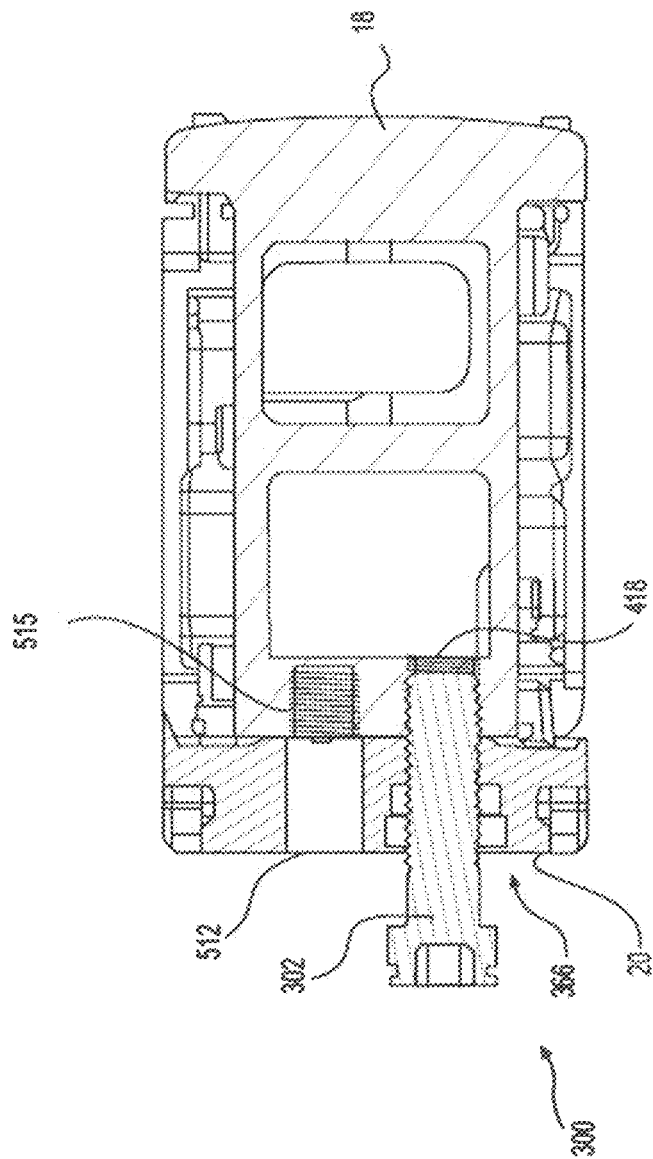
FIG. 19 is a cross-sectional view of an expandable fusion device according to another embodiment of the present disclosure.
Figure 20:
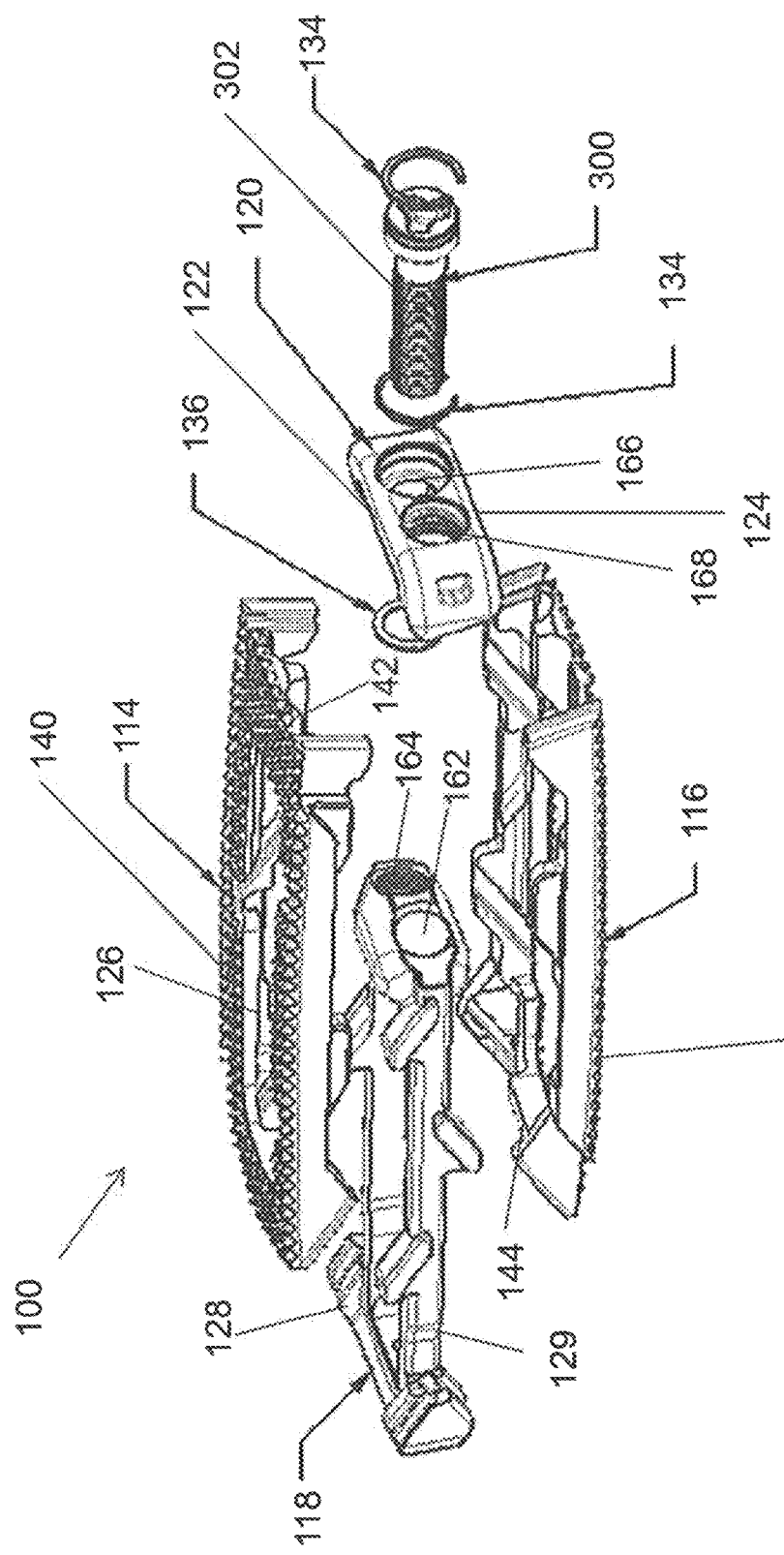
FIG. 20 is an exploded view of an expandable fusion device according to another embodiment of the present disclosure.
Figure 21:
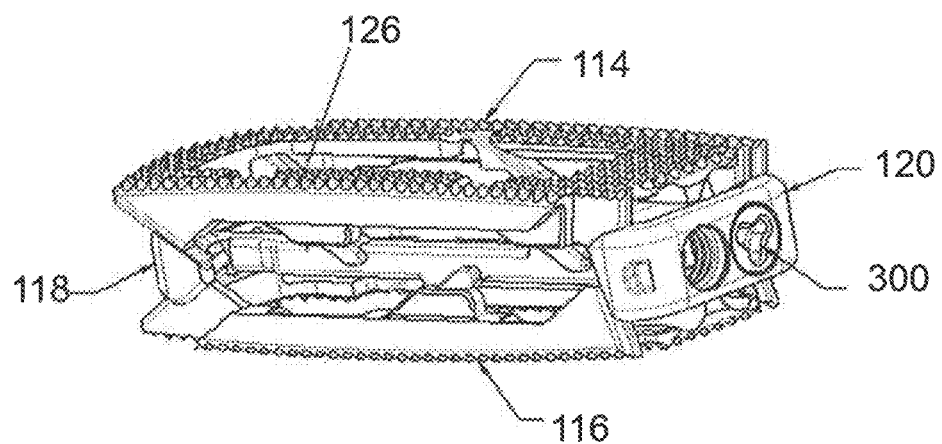
FIG. 21 is a perspective view of the expandable fusion device shown in FIG. 20.
Figure 22:
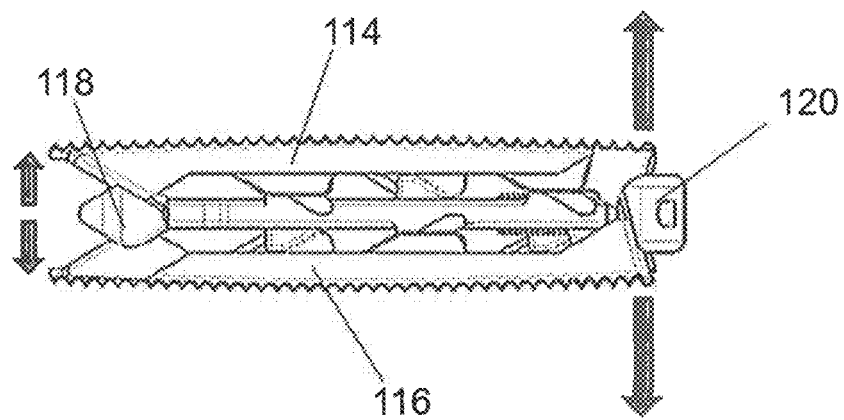
FIG. 22 is a side view of the expandable fusion device shown in FIG. 20 and depicting different rates of expansion between the front and back of the implant.

In an alternative embodiment shown in FIG. 19, threaded member 302 may be at least partially disposed within bore 515 in the collapsed configuration. However, to transition from the collapsed configuration to the expanded configuration, threaded member 302 may be actuated through second ramp 20. Unlike the embodiment shown in FIGS. 4 and 7, in the embodiment of FIG. 19, threaded member 302 may pull first ramp 18 toward second ramp 20, and may move coextensively with first ramp 18 during the transition of expandable fusion device 10 from the collapsed configuration to the expanded configuration and from the expanded configuration to the collapsed configuration. Any other suitable actuating mechanism may be utilized, such as, e.g., sliders, pushers, ratchets, or the like.

In some embodiments, threaded member 302 may be rotated directly to actuate the actuating mechanism 300. In some embodiments, an inserter (not shown) may be configured to thread into or be otherwise coupled to threaded member 302. In such embodiments, the inserter may be actuated by suitable mechanisms (e.g., tools, ratchets, or the like) to rotate threaded member 302 and adjust the relative position of the first and second ramps 18 and 20.

In some embodiments, only one of bores 366 and 418 may be threaded, such that expandable fusion device 10 may be actuated by linear movement of actuating mechanism 300. For example, in one embodiment, bore 366 may be threaded while bore 418 may not be threaded. In such an embodiment, threaded member 302 may be threaded into bore 366, and may be slidable through bore 418. After threaded member 302 is threaded through bore 366, threaded member 302 can be selectively pushed through bore 418 to move expandable fusion device 10 from the collapsed configuration to the expanded configuration (e.g., by moving first ramp 18 and second ramp 20 closer to one another). Additionally, threaded member 302 may be pulled in the opposite direction to move expandable fusion device 10 from the collapsed configuration to the expanded configuration (e.g., by moving first ramp 18 and second ramp 20 away from one another). In this embodiment, second ramp 20 may be pushed toward first ramp 18 to move expandable fusion device 10 from the collapsed configuration to the expanded configuration.

In an alternative embodiment, bore 418 may be threaded and bore 366 may not be threaded. In such an embodiment, threaded member 302 may be disposed through bore 366 and threaded into bore 418 (e.g., referring to FIG. 19). Threaded member 302 may be pulled linearly to move expandable fusion device 10 from the collapsed configuration to the expanded configuration (e.g., by moving first ramp 18 and second ramp 20 closer to one another). Additionally, threaded member 302 may be pushed to move expandable fusion device 10 from the expanded configuration back to the collapsed configuration (e.g., by moving first ramp 18 and second ramp 20 away from one another). In this embodiment, first ramp 18 may be pulled toward second ramp 20 to move expandable fusion device 10 from the collapsed configuration to the expanded configuration.

In one embodiment, a locking member (e.g., a screw not shown) may be disposed separately of expandable fusion device 10 during the transition between the collapsed and expanded configurations. Once the final position is achieved (e.g., the expanded configuration of expandable fusion device 10), the locking member may be advanced to lock expandable fusion device 10 into a desired configuration. In some embodiments, the locking member may be integral with expandable fusion device 10, or may be alternatively introduced after expansion. In some embodiments, the locking member may be captured within the expandable fusion device 10 so that it is not lost. In some embodiments, peening the tip of the locking member may prevent the locking member from becoming lost.

Once expandable fusion device 10 has been moved to the expanded configuration and locked via the locking member, bores 366 and 418, previously used to expand the expandable fusion device 10 via actuating mechanism 300 may be utilized to pack graft or other bone growth inducing substances into expandable fusion device 10. That is, bores 366 and 418 may be utilized to pack graft into the expandable fusion device 10 to fill any potential gaps that formed during expansion of expandable fusion device 10.

With reference to FIGS. 20-24, an embodiment of expandable fusion device 100 is shown. In an exemplary embodiment, the expandable fusion device 100 may include a first endplate 114, a second endplate 116, a first ramp 118, and a second ramp 120. The first and/or second endplates 114, 116 of the expandable fusion device 100 may include one or more openings 126 to accommodate bone growth and/or bone growth materials.

The first endplate 114 includes an outer surface 140 configured to engage an adjacent vertebral body and an inner surface 142 configured to mate with at least a portion of the first and second ramps 118, 120. The second endplate 116 includes an outer surface 145 configured to engage an adjacent vertebral body and an inner surface 144 configured to mate with at least a portion of the first and second ramps 118, 120. The first ramp 118 includes an upper portion 128, which is sized to receive at least a portion of the first endplate 114, and a lower portion 129, which is sized to receive at least a portion of the second endplate 116. The second ramp 120 may be disposed adjacent to the first ramp 118. The second ramp 120 includes an upper portion 122, which is sized to contact at least a portion of the first endplate 114, and a lower portion 124, which is sized to contact at least a portion of the second endplate 116. The first and/or second ramps 118, 120 may include any of the mating features described herein.

The first ramp 118 may include one or more bores 162, 164. The second ramp 120 may include a bore 166 adjacent bore 168. The bore 166 may be configured to receive an actuating mechanism 300 therethrough, and may be aligned with the bore 164 in the first ramp 118. The bores 164, 166 may be threaded, such that expandable fusion device 100 may be actuated by linear movement of the actuating mechanism 300. The actuating mechanism 300 may include a threaded member 302 as described above. The actuating mechanism may also include one or more snap rings 134 and/or washers 136. The snap rings 134 and washers 136 may be formed from any suitable material, such as titanium, PEEK, or the like. After threaded member 302 is threaded through bore 166, threaded member 302 can be selectively threaded through bore 164 to move the expandable fusion device 100 from the collapsed configuration to the expanded configuration (e.g., by moving first ramp 118 and second ramp 120 closer to one another).

Accordingly, expandable fusion device 100 may be movable between a collapsed configuration and an expanded configuration as described herein. After the expandable fusion device 100 has been inserted into the appropriate position in the intervertebral disc space, the expandable fusion device 100 can then be transitioned from the collapsed configuration to the expanded configuration. To expand the expandable fusion device 100, the second ramp 120 may be moved toward the first ramp 118. As the first and second ramps 118 and 120 move toward one another, the respective mating features of first and second ramps 118 and 120 may push against corresponding mating features disposed on endplates 114 and 116 to move the expandable fusion device 100 into the expanded configuration. Thus, the expandable fusion device 100 is able to reciprocally move between the collapsed and expanded configurations.

Depending on the expansion profile desired, symmetrical or asymmetrical expansion of the device 100 may be required. Even if symmetrical expansion is preferred, however, expandable implants that utilize ramps for expansion may be subject to inconsistent expansion rates. For example, depending on the slope of the ramp interface or shape of the mating features, the endplates 114, 116 may expand at a faster rate at the back of the implant as opposed to the front of the implant. This is shown, for example, in FIG. 22 where the arrows depict the relative rates of expansion. By making the front ramp angles different from the back angles, the asymmetrical expansion issue may be alleviated. For example, increasing the front ramp angles and decreasing the back ramp angles ensures that the endplates 114, 116 expand symmetrically.

Figure 23:
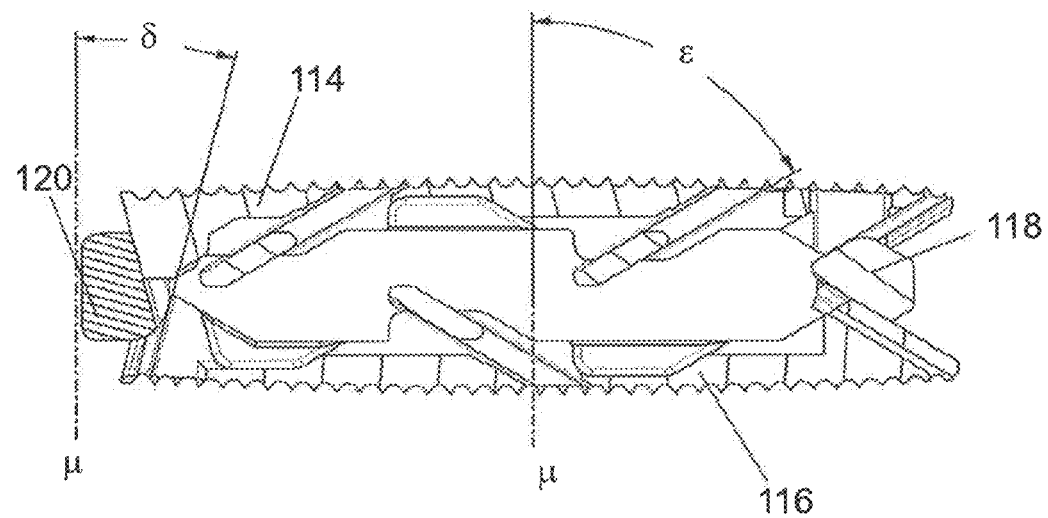
FIG. 23 shows a cross sectional view of the expandable fusion device shown in FIG. 20 including the ramp angles.
Figure 24:
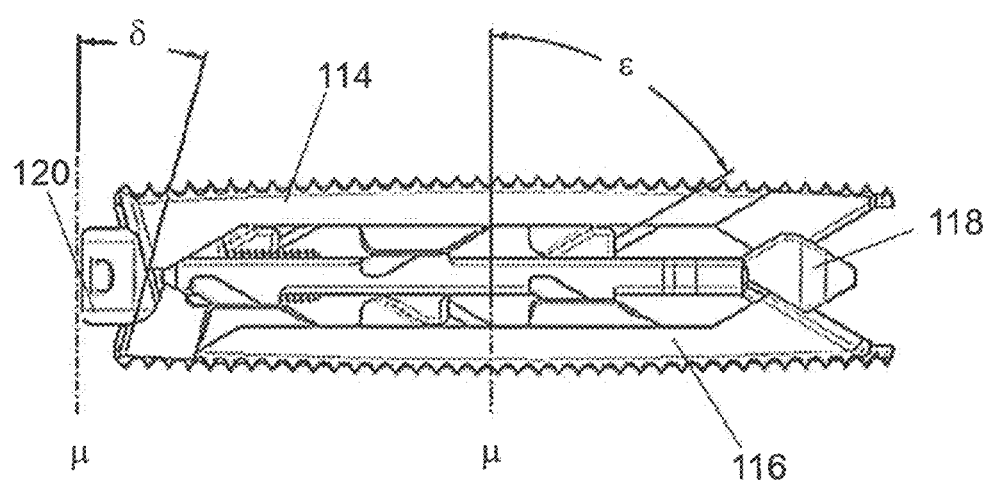
FIG. 24 is a side view of the expandable fusion device shown in FIG. 20 and depicting the ramp angle.

The front and back ramp angles may be the same or different. As shown in FIGS. 23 and 24, an angle $\epsilon$ is provided for the front ramp angles (e.g., the angle(s) on the mating features of the first ramp 118), and an angle $\delta$ is provided for the back ramp angles (e.g., the angle(s) on the mating feature of the second ramp 120). These angles $\epsilon$, $\delta$ are measured from the vertical axis $\mu$. The angle $\epsilon$ may be provided on the mating surfaces for the first ramp 118, the first endplate 114, and/or the second endplate 116, respectively. The angle $\delta$ may be provided on the mating surfaces for the second ramp 120, the first endplate 114, and/or the second endplate 116, respectively. The angle $\epsilon$ is preferably larger than the angle $\delta$, for example, at a ratio of about 4:1. The angle $\epsilon$ may range from about 50-70°, 55-65°, 57-63°, 58-62°, or 59-61°. In a preferred embodiment, angle $\epsilon$ is 60°. The angle $\delta$ may range from about 5-25°, 10-20°, 12-18°, 13-17°, 14-16°. In a preferred embodiment, angle $\delta$ is 15°. Increasing the angle $\epsilon$ and decreasing the angle $\delta$ in this manner ensures that the endplates 114, 116 expand symmetrically. By expanding symmetrically, the endplates 114, 116 are able to contact the vertebral body endplates appropriately and maintain anatomical balance in situ. Although a symmetrical expansion is described, an asymmetrical expansion may also be contemplated. The angles $\epsilon$, $\delta$ may be changed or adjusted to provide for asymmetrical expansion of the endplates 114, 116.

Figure 25:
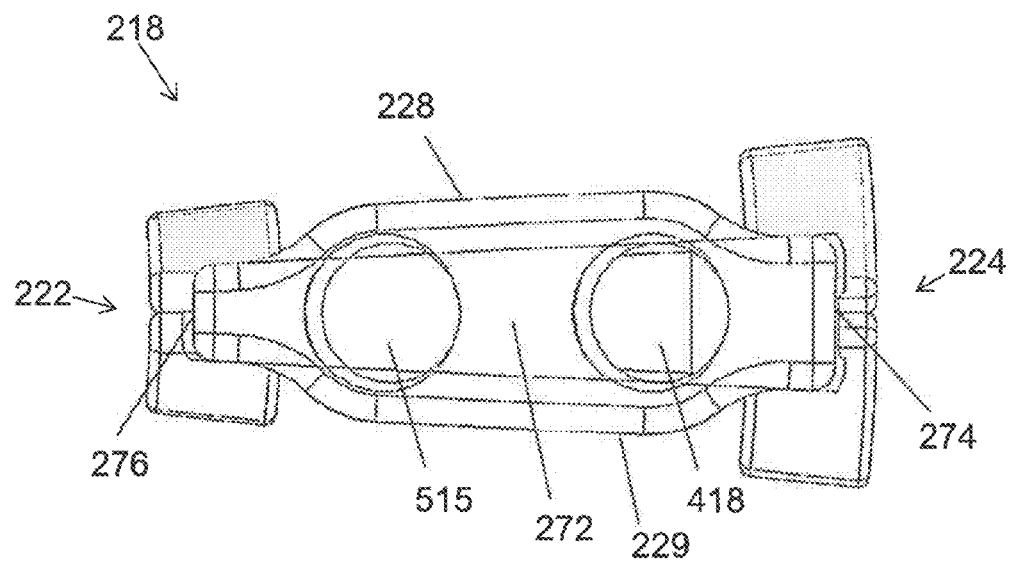
FIG. 25 is a front view of the front, first ramp which may be used with any of the expandable fusion devices described herein.
Figure 26:
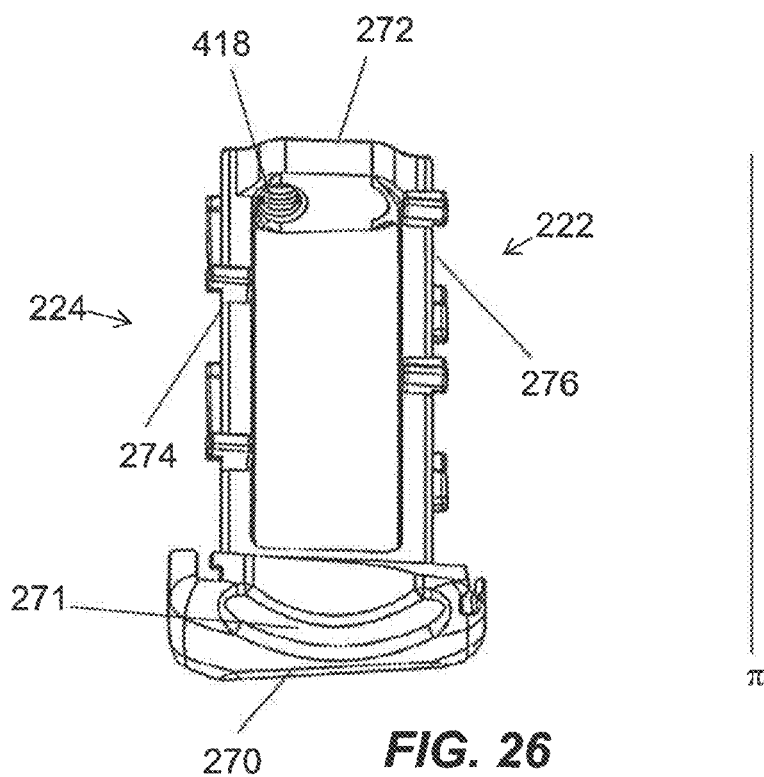
FIG. 26 is a top view of the first ramp shown in FIG. 25.

With reference to FIGS. 25 and 26, an embodiment of a first, front ramp 218 is shown, which is suitable for use with any of the expandable fusion devices described herein. The first ramp 218 may have a first end 270 on an insertion end of the device, a second end 272 configured to mate with the second ramp 20, 120, a first side portion 274, and a second side portion 276 on the opposing side of the first ramp 218. The first ramp 218 may extend generally from a first side 222 (e.g., a posterior side) to a second side 224 (e.g., an anterior side). The first ramp 218 may be generally wedge shaped, and may have a height that increases from the first side 222 toward the second side 224. The first ramp 218 may further include an upper portion 228, which is sized to receive at least a portion of the first endplate 14, 114, and a lower portion 229, which is sized to receive at least a portion of the second endplate 16, 116. As discussed above, the second end 272 of the first ramp 218 may include bores 418, 515. In some embodiments, the bore 418 may be configured to receive the threaded member 302 of the actuating mechanism 300. The adjacent bore 515 may serve as an access port to allow graft material to be delivered through the first ramp 218 prior to insertion or in situ.

The first ramp 218 may have a curvature or pitch on at least one ramp surface or mating feature. For example, the first end 270 may have a curved ramp surface 271. The second or anterior side 224 may have a higher ramp angle than the first or posterior side 222 or vice versa. One or more portions of the first ramp 218 including one or more of the ramp surfaces or mating features may include a continuously changing ramp angle. The continuous linear change of the implant's angle (e.g., lordotic angle) may be contingent on a continuously changing ramp angle. This results in a curvature of the ramp surface which can be defined by angular change per distance away from the pivot axis $\pi$. This value is the pitch of the implant ramp surfaces, and is responsible for varying the rate of angular change the implant is able to achieve. A larger pitch value correlates to a higher ramp angle at the anterior ramp edge in relation to the angle at the posterior ramp edge for an implant of fixed width. The mating features, ramp angles, type of angle change, lordotic angle, rate of expansion, and the like may be configured as described herein to provide for optimal design and functionality of the device.

Figure 27A:
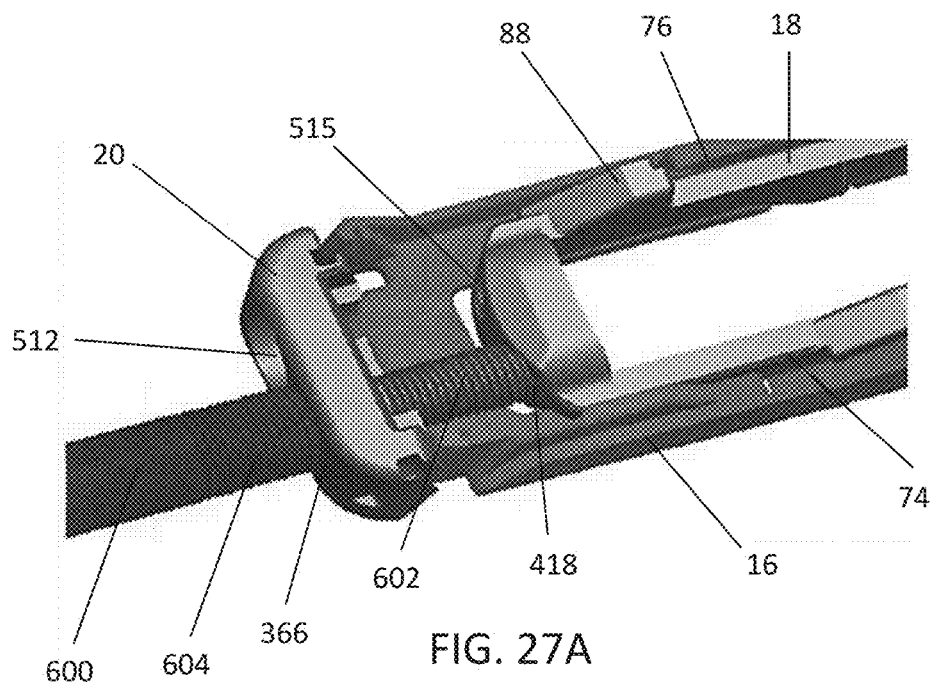
FIGS. 27A and 27B show an insertion instrument engaged with any of the expandable fusion devices described herein.
Figure 27B:
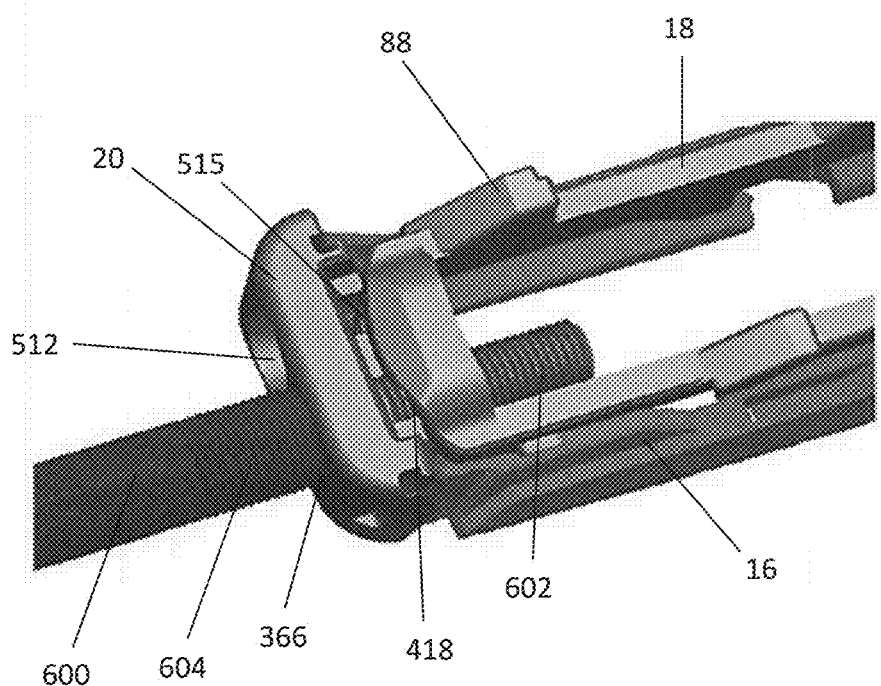

Referring now to FIGS. 27A and 27B, an inserter instrument 600 may allow for adjustment of implant height and/or lordotic angle, for example, via insertion of a threaded shaft 602 contained within the instrument 600, which may be removed once the implant height and lordotic angle are set. FIGS. 27A and 27B show a portion of expandable fusion device 10 with the first endplate removed, but the instrument 600 and methods described herein may be suitable for use with any expandable fusion device.

The instrument 600 includes a threaded inner shaft 602, which when inserted through the back of the expandable fusion device 10, rigidly connects to the first ramp 18, for example, using a threaded connection or other similar feature. The instrument 600 may also include a threaded outer shaft 604, which is configured to rigidly connect to the second ramp 20, for example, using a threaded connection or other similar feature. By rotating and/or axially moving the inner shaft 602 relative to the outer shaft 604 of the instrument 600, the first ramp 18 is drawn toward the back of the expandable fusion device 10, causing a change in height and/or lordotic angle. In other words, the first and second ramps 18, 20 are drawn toward or away from one another by axially moving the inner shaft 602 relative to the outer shaft 604 of the instrument 600.

In an alternative embodiment, the inserter instrument 600 can be used in conjunction with the threaded member 302 of the actuating mechanism 300 described herein. For example, the instrument 600 may be threaded into the threaded hole opposite to the threaded member 302. For example, the openings 366, 512 in the second ramp 20 may be threaded and the openings 418, 515 in the first ramp 18 may be threaded. The openings 366, 418 may be generally aligned and the openings 512, 515 may be generally aligned. Accordingly, the inserter instrument 600 may be placed into one set of openings (e.g., openings 366, 418 as shown) and the threaded member 302 may be positioned in the other set of openings (e.g., openings 512, 515). For example, the inner shaft 602 may rigidly connect to the opening 418 in the first ramp 18 and the outer shaft 604 may rigidly connect to the opening 366 in the second ramp 20.

Once coupled to the device 10, the instrument 600 is configured to linearly pull or push the first ramp 18 to expand or contract the expandable fusion device 10. After expansion, the threaded member 302 may be rotated into position to lock the relative positions of the first and second ramps 18, 20 relative to one another. For example, the threaded member 302 may back up or move away from the first ramp 18 as the instrument 600 is utilized to expand the expandable fusion device 10. Once the final position is achieved (e.g., height and lordotic angle), the threaded member 302 is advanced to lock the final height and lordotic angle of the endplates 14, 16 into position. The threaded member 302 can be integral with the device 10 or can be introduced after expansion. If integral, the threaded member 302 may be secured, for example, to the first or second ramp 18, 20 by peening or the like.

Once the expandable fusion device 10 has been expanded and locked, the openings 418, 366, 515, 512 where the instrument 600 was used to expand the device 10, which has subsequently been removed, may be filled and packed with bone graft. In addition, if accessible, the graft material can be packed through any of the openings 418, 366, 515, 512 and into the device 10 to fill any potential gaps that were created during expansion.

Any aspect set forth in any embodiment may be used with any other embodiment set forth herein. Every device and apparatus set forth herein may be used in a suitable medical procedure, such as, e.g., a vertebral disc replacement procedure, and may be advanced through any suitable body lumen and body cavity.

It will be apparent to those skilled in the art that various modifications and variations can be made in the disclosed systems and processes without departing from the scope of the disclosure. Other embodiments of the disclosure will be apparent to those skilled in the art from consideration of the specification and practice of the disclosure disclosed herein. It is intended that the specification and examples be considered as exemplary only. The following disclosure identifies some other exemplary embodiments.

We claim:

1. A system comprising:
an expandable fusion device comprising:
a first endplate having an upper surface defining a first plane extending from a first side of the expandable fusion device to a second side of the expandable fusion device, and a second endplate having a lower surface defining a second plane extending from the first side of the expandable fusion device to the second side of the expandable fusion device, wherein the first and second endplates each include at least one mating feature;
a first ramp including at least one opening and mating features configured to mate with the at least one mating features of the first and second endplates, wherein the first ramp is slidable with respect to the first and second endplates;
a second ramp including at least one opening generally aligned with the at least one opening in the first ramp and mating features configured to mate with the at least one mating features of the first and second endplates; and
a threaded member configured to engage a corresponding opening in each of the first ramp and the second ramp to lock a position of the first ramp relative to a position of the second ramp,
wherein the expandable fusion device is movable between a collapsed configuration and an expanded configuration and in the collapsed configuration the first plane and the second plane are non-parallel; and
an inserter instrument comprising:
an outer shaft having a bore extending longitudinally therethrough, the outer shaft configured to engage the at least one opening in the second ramp; and
an inner shaft extending through the bore in the outer shaft, the inner shaft configured to engage the at least one opening in the first ramp.

2. The system of claim 1, wherein the inner shaft of the inserter instrument is threaded, and the inner shaft threadedly engages the at least one opening in the first ramp.

3. The system of claim 1, wherein the outer shaft of the inserter instrument is threaded, and the outer shaft threadedly engages the at least one opening in the second ramp.

4. The system of claim 1, wherein the inner shaft is configured to axially move through the outer shaft of the inserter instrument.

5. The system of claim 1, wherein the upper surface and the lower surface are configured to contact a respective vertebral body, wherein the upper surface and the lower surface of the first and second endplates has one or more of teeth, ridges, friction increasing elements, keels, or gripping or purchasing projections.

6. The system of claim 1, wherein a central longitudinal axis of the first opening is off-center from a central longitudinal axis of the first ramp.

7. A system comprising:
an expandable fusion device comprising:
a first endplate having an upper surface defining a first plane extending from a first side of the expandable fusion device to a second side of the expandable fusion device, and a second endplate having a lower surface defining a second plane extending from the first side of the expandable fusion device to the second side of the expandable fusion device, wherein the first and second endplates each include at least one mating feature;
a first ramp including first and second openings and mating features configured to mate with the at least one mating features of the first and second endplates, wherein the first ramp is slidable with respect to the first and second endplates;
a second ramp including first and second openings and mating features configured to mate with the at least one mating features of the first and second endplates, the first opening generally aligned with the first opening in the first ramp, and the second opening generally aligned with the second opening in the second ramp;
a threaded member configured to engage a corresponding opening in each of the first ramp and the second ramp to lock a position of the first ramp relative to a position of the second ramp,
wherein the expandable fusion device is movable between a collapsed configuration and an expanded configuration and in the collapsed configuration the first plane and the second plane are non-parallel; and an inserter instrument comprising:
an outer shaft having a bore extending longitudinally therethrough, the outer shaft configured to engage the first or second opening in the second ramp; and
an inner shaft extending through the bore in the outer shaft, the inner shaft configured to engage the corresponding first or second opening in the first ramp.

8. The system of claim 7, wherein the first and second openings of the first ramp are threaded.

9. The system of claim 8, wherein the inner shaft of the inserter instrument is threaded, and the inner shaft threadedly engages the first opening in the first ramp.

10. The system of claim 7, wherein the first and second openings of the second ramp are threaded.

11. The system of claim 10, wherein the outer shaft of the inserter instrument is threaded, and the outer shaft threadedly engages the first opening in the second ramp.

12. The system of claim 7, wherein the inner shaft is configured to axially move through the outer shaft of the inserter instrument.

13. A system comprising:
an expandable fusion device comprising:
a first endplate having an upper surface defining a first plane extending from a first side of the expandable fusion device to a second side of the expandable fusion device, and a second endplate having a lower surface defining a second plane extending from the first side of the expandable fusion device to the second side of the expandable fusion device, wherein the first and second endplates each include mating features;
a first ramp including first and second openings and mating features configured to mate with the mating features of the first and second endplates, wherein the first ramp is slidable with respect to the first and second endplates;
a second ramp including first and second openings and mating features configured to mate with the mating features of the first and second endplates, the first opening generally aligned with the first opening in the first ramp, and the second opening generally aligned with the second opening in the second ramp; and
a threaded member configured to engage a corresponding opening in each of the first ramp and the second ramp to lock a position of the first ramp relative to a position of the second ramp,
wherein the expandable fusion device is movable between a collapsed configuration and an expanded configuration and in the collapsed configuration the first plane and the second plane are non-parallel; and
an inserter instrument comprising:
an outer shaft having a bore extending longitudinally therethrough, the outer shaft having a threaded outer surface extending through the other of the first or second openings in the second ramp; and
an inner shaft extending through the bore in the outer shaft, the inner shaft having a threaded outer surface extending through the corresponding first or second opening in the first ramp.

14. The system of claim 13, wherein the first and second openings of the first ramp are threaded.

15. The system of claim 13, wherein the first and second openings of the second ramp are threaded.

16. The system of claim 13, wherein the inner shaft is configured to axially move through the outer shaft of the inserter instrument.

* * * * *